United States Patent [19]

Osipov

[11] Patent Number: 5,014,970

[45] Date of Patent: May 14, 1991

[54] BODY MEMBER POSITIONER

[75] Inventor: Vladimir W. Osipov, Barre, Mass.

[73] Assignee: Walker Magnetics Group, Inc., Worcester, Mass.

[21] Appl. No.: 531,911

[22] Filed: May 31, 1990

[51] Int. Cl.$^5$ .............................................. A61G 13/00
[52] U.S. Cl. ................................................... 269/328
[58] Field of Search ..................... 269/328, 20, 22; 254/93 HP; 128/134, 133, 1 R, DIG. 20, 80 R, 327, 64

[56] References Cited

U.S. PATENT DOCUMENTS

| | | | |
|---|---|---|---|
| 1,374,295 | 4/1921 | Fleury | 254/93 HP |
| 3,924,843 | 12/1975 | Hirmann | 254/93 HP |
| 4,232,681 | 11/1980 | Tulaszewski | 269/328 |
| 4,299,213 | 11/1981 | Violet | 269/328 |
| 4,526,355 | 7/1985 | Moore et al. | 269/328 |
| 4,620,698 | 11/1986 | Reed et al. | 269/328 |
| 4,766,892 | 8/1988 | Kreitman | 269/328 |
| 4,774,959 | 10/1988 | Palmer et al. | |

Primary Examiner—Robert C. Watson
Attorney, Agent, or Firm—Henry D. Pahl, Jr.

[57] ABSTRACT

The body member positioning apparatus disclosed herein operates to clamp a body member, such as a foot, in relation to a fixture, e.g. such as may be used for ultrasonic bone testing. A shell member is provided which conforms to the expected shape of the body member with a space therebetween, this space being filled with a compliant foam liner. An inflatable bladder or bellows operates between a stationary housing part and a movable housing part to which the shell member is attached so that, by inflating the bladder, a clamping pressure can be exerted against a body member positioned between the shell and the fixture.

2 Claims, 1 Drawing Sheet

BODY MEMBER POSITIONER

BACKGROUND OF THE INVENTION

The present invention relates to positioning apparatus and more particularly to an apparatus for clamping a body member in relation to a fixture.

For certain types of medical testing, it is important that a body member be reliably restrained or held in position relative to a test fixture during the testing. For example, in the ultrasonic testing of bone condition, it is important that the subject's heel be accurately and reproducibly positioned in a fixture which includes a pair of transducers which are to be positioned on opposite sides of the heel, preferably in alignment with the calcancous. Ultrasonic bone testing apparatus is, for example, disclosed in U.S. Pat. No. 4,774,959 issued on Oct. 4, 1988 to Palmer et al. and entitled Narrow Band Ultrasonic Frequency Attenuation Bone Measurement System. The disclosure of said patent is incorporated herein by reference.

Among the several objects of the present invention may be noted the provision of novel apparatus for clamping a body member in relation to a fixture; the provision of such apparatus which will essentially prevent movement of the body member; the provision of such apparatus which will allow the body member to be positioned reproducibly; the provision of such apparatus which does not cause discomfort to the patient whose body member is being positioned; the provision of such apparatus which is reliable and which is of relatively simple and inexpensive construction. Other objects and features will in part be apparent and in part pointed out hereinafter.

SUMMARY OF THE INVENTION

Apparatus constructed in accordance with the present invention is operative to clamp a body member in relation to a fixture. A shell member is utilized which is shaped to conform to a surface which is spaced from the nominal or expected configuration of the body member. The shell member is lined with a compliant foam having a relaxed thickness greater than the spacing. An inflatable bladder is contained in an expandable housing having a stationary housing part adapted to be attached to the fixture and a movable part to which the shell member is attached. By inflating the bladder, a clamping pressure is exerted against a body member positioned between the shell and the fixture.

BRIEF DESCRIPTION OF THE DRAWINGS

Corresponding reference characters indicate corresponding parts throughout the several views of the drawings.

DESCRIPTION OF THE PREFERRED EMBODIMENT

As indicated previously, the particular configuration described herein is adapted to be used with an ultrasonic bone analyzer of the type disclosed in U.S. Pat. No. 4,774,959. As described in that patent, the bone analysis is performed by transmitting ultrasonic energy through the patient's heel, particularly the os calcis, and by measuring the transmission characteristics as a function of frequency. During the measurement, the patient's heel and the transducers are immersed in a liquid to facilitate the coupling of the ultrasonic energy.

Figure 1:
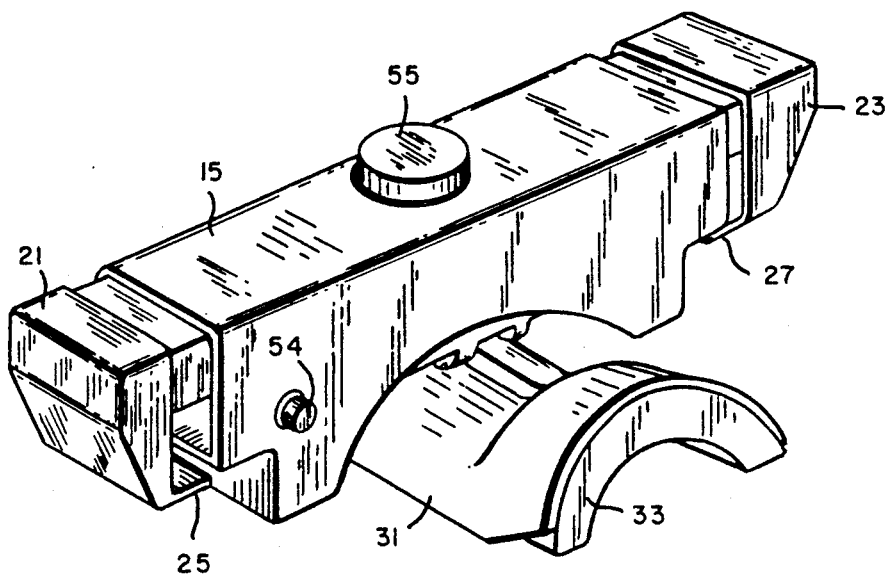
FIG. 1 is a view, in perspective, of clamping apparatus in accordance with the present invention.
Figure 2:
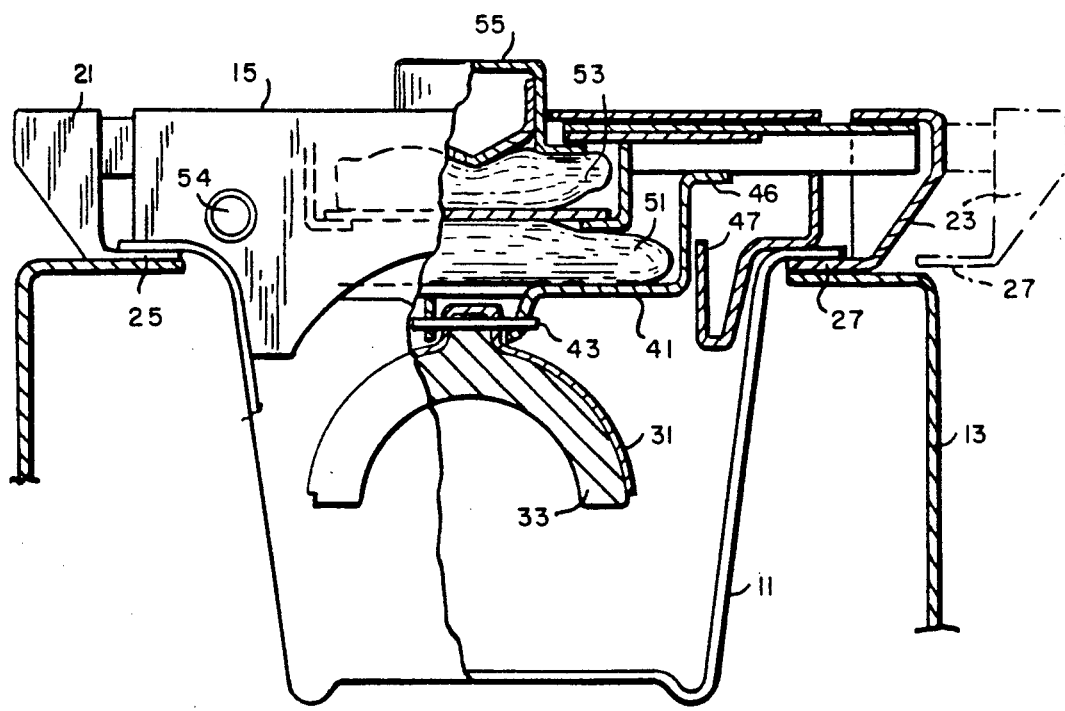
FIG. 2 is a back view, largely in section, showing the clamping apparatus of FIG. 1 mounted on an ultrasonic bone analyzer scanning unit.

Referring now to the drawings, the current implementation of the scanning unit employs an inner liner 11 and scanner enclosure 13 as indicated in FIG. 2. To cooperate with this arrangement, the stationary housing or frame of the clamping apparatus of the present invention is configured as a bridge 15 which straddles the inner liner 11. Brackets 21 and 23 which can be extended by sliding from sockets on either side of the bridge 15 include hook portions 25 and 27 which can be hooked under the rim of the inner liner 11 so as to prevent upward movement of the bridge member when clamping force is exerted as described hereinafter.

A shell member 31 is employed which is shaped to conform to a surface spaced from the nominal expected configuration of the body member, in this case, a human foot. The shell is lined with a compliant plastic foam as indicated by reference character 33. The relaxed thickness of the foam lining is somewhat greater than the designed spacing between the shell member and the expected configuration of the body member so that when clamping force is exerted a distributed pressure is exerted over the foot by the compressed foam.

Associated with the stationary housing part 15 is a movable housing part. The movable part of the expandable housing is a somewhat tray-like structure designated generally by reference character 41. The movable housing part slides within the stationary housing part thereby to form an expandable chamber or compartment between the two housing parts. The range of movement of the movable part 41 is limited by an upper lip 46 on the movable housing part and a corresponding lip 47 on the lower part of the bridge element 15. The shell member 31 is pivotally attached to the lower side of the movable housing part by a pin as indicated by reference character 43. The housing parts, the clamp bars and brackets, and the shell 31 are preferably constructed of thermoformed ABS plastic resin with elements being cemented together as necessary.

An inflatable bladder 51 is positioned between the stationary and movable housing parts as shown in FIG. 2. The term bladder is intended to include bellows and other equivalent elements. A bulb pump 53 and a release valve 54 are provided for controlling the air pressure in the bladder, these elements being interconnected by appropriate tubing, not shown.

In use, the brackets are expanded and the bridge member 15 is removed from the inner liner 11 to allow a subject to insert a foot into the fixture. With the bladder deflated, the bridge is then replaced and clamped in position with the shell member merely resting on the upper portion of the subject's foot. By then inflating the bladder using the manual pump 53, a clamping pressure can be exerted downwardly which presses the subject's heel into the fixture with a distributed pressure exerted through the compliant foam 33. This method of clamping has been found to provide highly accurate, reliable and consistently reproducible positioning of the foot for ultrasonic testing.

In view of the foregoing it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

What is claimed is:

1. Apparatus for clamping a subject's foot downwardly within a tray-like fixture having a cavity for receiving the foot, said apparatus comprising:

a shell member shaped to conform to a surface which is spaced from the nominal expected configuration of the upper portion of the patient's foot;

a compliant foam lining said shell member and having a relaxed thickness greater than said spacing;

an expandable housing containing said bladder, said housing including a stationary bridge part adapted to be attached to said fixture spanning the tray cavity and a movable housing part to which said shell member is pivotally attached;

between said bridge part and said movable part, an inflatable bladder;

means for inflating said bladder thereby exerting a clamping pressure against a subject's foot positioned between said shell and said fixture.

2. Apparatus as set forth in claim 1 wherein said tray-like fixture includes an outwardly extending rim and wherein said bridge part includes sockets for receiving brackets which engage said rim, securing said bridge member.

* * * * *